| United States Patent [19] | [11] Patent Number: 4,812,405 |
| Lair et al. | [45] Date of Patent: Mar. 14, 1989 |

[54] **DOUBLE AUXOTROPHIC MUTANTS OF *PICHIA PASTORIS* AND METHODS FOR PREPARATION**

[75] Inventors: Stephen V. Lair, La Jolla; Mary E. Digan, San Diego, both of Calif.

[73] Assignee: Phillips Petroleum Company, Bartlesville, Okla.

[21] Appl. No.: 830,304

[22] Filed: Feb. 18, 1986

[51] Int. Cl.$^4$ .......................... C12N 1/16; C12N 15/00; C12R 1/84

[52] U.S. Cl. ..................................... 435/255; 435/938; 435/172.1; 435/172.3; 935/69; 935/79; 935/97

[58] Field of Search ................... 435/172.1, 172.3, 171, 435/224, 255, 938, 190, 232; 935/69, 79, 97

[56] References Cited

U.S. PATENT DOCUMENTS 4,172,764 10/1979 Heslot et al. ........................ 435/172
4,375,515 3/1983 Patel et al. ........................... 435/189

FOREIGN PATENT DOCUMENTS 0060057 9/1982 European Pat. Off. .

OTHER PUBLICATIONS

Advances in Protoplast Research, pp. 99–104, 113–118, L. Ferenczy and G. L. Farkas, eds.; Pergamon Press, New York.
Kuntze et al., Current Genetics (1985) 9, 205–209.
Cregg et al., Mol. and Cell Biol. (1985) 5, 3376–3385.
Herrman et al., Amino Acid Biosyntheses and Genetic Reg., 1983.

*Primary Examiner*—Elizabeth C. Weimar
*Assistant Examiner*—Patricia Carson
*Attorney, Agent, or Firm*—J. E. Phillips

[57] ABSTRACT

Processes for the preparation of double auxotrophic mutants of *Pichia pastoris* are provided, as well as novel double auxotrophic mutant strains produced thereby.

2 Claims, No Drawings

DOUBLE AUXOTROPHIC MUTANTS OF *PICHIA PASTORIS* AND METHODS FOR PREPARATION

This invention relates to the field of recombinant DNA technology. In one of its aspects, the invention relates to novel yeast strains. In another aspect, the invention relates to processes for producing novel yeast strains.

BACKGROUND

Up to now, commercial efforts employing recombinant DNA technology for producing various polypeptides have centered as *Escherichia coli* as a host organism. However, in some situations *E. coli* may prove to be unsuitable as a host. For example, *E. coli* contains a number of toxic pyrogenic factors that must be eliminated from any polypeptide useful as a pharmaceutical product. The efficiency with which this purification can be achieved will, of course, vary with the particular polypeptide. In addition, the proteolytic activities of *E. coli* can seriously limit yields of some useful products. These and other considerations have led to increased interest in alternative hosts, in particular, the use of eukaryotic organisms for the production of polypeptide products is appealing.

The availability of means for the production of polypeptide products in eukaryotic systems, e.g., yeast, could provide significant advantages relative to the use of prokaryotic systems such as *E. coli* for the production of polypeptides encoded by recombinant DNA. Yeast has been employed in large scale fermentations for centuries, as compared to the relatively recent advent of large scale E. coli fermentations. Yeast can generally be grown to higher cell densities than bacteria and are readily adaptable to continuous fermentation processing. In fact, growth of yeast such as *Pichia pastoris* to ultra-high cell densities, i.e., cell densities in excess of 100 g/L, is disclosed by Wegner in U.S. Pat. No. 4,414,329 (assigned to Phillips Petroleum Co.). Additional advantages of yeast hosts include the fact that many critical functions of the organism, e.g., oxidative phosphorylation, are located within organelles, and hence are not exposed to the possible deleterious effects of the organism's production of polypeptides foreign to the wild-type host cells. As a eukaryotic organism, yeast may prove capable of glycosylating expressed polypeptide products where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA (cDNA) obtained by reverse transcription from, for example, mammalian mRNA.

The development of poorly characterized yeast species as host/vector systems is severely hampered by the lack of knowledge about transformation conditions and suitable vectors. In addition, auxotrophic mutations are often not available, precluding a direct selection for transformants by auxotrophic complementation. Moreover, where auxotrophic mutants are available, it is often not possible to prepare double auxotrophic mutants by mating procedures since mating protocols are unknown or do not exist for some yeast strains. Double auxotrophic mutants are desirable host organisms because they allow a variety of selection pressures and conditions to be used for strain manipulation.

If recombinant DNA technology is to fully sustain its promise, new host/vector systems must be devised which facilitate the manipulation of DNA as well as optimize expression of inserted DNA sequences so that the desired polypeptide products can be prepared under controlled conditions and in high yield.

OBJECTS OF THE INVENTION

An object of the present invention, therefore, is the preparation of novel double auxotrophic mutants of the species *Pichia pastoris*.

Another object of the invention is the development of methods for the preparation of double auxotrophic mutants of yeasts of the species *Pichia pastoris*.

These and other objects of the invention will become apparent from inspection of the disclosure and claims herein provided.

STATEMENT OF THE INVENTION

In accordance with the present invention, there have been developed processes for the preparation of double auxotrophic mutants of yeast strains of the species *Pichia pastoris*.

Further in accordance with the present invention, novel double auxotrophic mutant strains of microorganisms of the species *Pichia pastoris* are provided. Such double auxotrophic mutants have not previously been available. Double auxotrophic mutants are useful hosts for transformation with recombinant DNA material.

DETAILED DESCRIPTION OF THE INVENTION

In accordance with the present invention, yeast cells of the species *Pichia pastoris* which are capable of being transformed with recombinant DNA material are provided. The yeast cells of the present invention have two distinct defects in their biosynthetic pathways relative to wild-type cells of the species *Pichia pastoris*. The yeast cells of the present invention are useful, in one respect, as host cells for recombinant DNA material.

Further in accordance with one embodiment of the present invention, a cell fusion process for producing double auxotrophic mutants of yeast strains of the species *Pichia pastoris* is provided. The cell fusion process of the invention comprises the following steps:

(a) contacting a first and a second monoauxotrophic mutant yeast strain of the species *Pichia pastoris* with both a sulfhydryl group reducing agent and a cell wall degrading reagent under conditions suitable for the formation and maintenance of spheroplasts;

(b) combining the spheroplasts prepared in accordance with step (a) to produce a mixture of spheroplasts, then contacting said mixture of spheroplasts with a cell fusion promoting agent;

(c) incubating the mixture of spheroplasts prepared in accordance with step (b) under cell wall regenerating conditions to produce a collection of prototrophic colonies;

(d) plating the prototrophic colonies produced in accordance with step (c) on presporulation agar and maintaining the resulting plates at about 30° C. for 12–48 hours;

(e) replica plating the cells produced in accordance with step (d) onto sporulation agar and maintaining the resulting plates at about 30° C. for 3–5 days;

(f) alternatively (1) dissecting the 4-spored asci produced in accordance with step (e); or (2) removing the cells from the sporulation plates, resuspending the cells in phosphate buffered media and exhaustively digesting the suspended cells with a cell wall degrading reagent;

(g) then germinating and growing each spore in rich media at about 25°-35° C. for 2-5 days; and (h) screening the collection of cells prepared in accordance with steps (a)-(g) for double auxotrophic mutants; and (i) isolating the double auxotrophic mutants from the collection of cells screened in accordance with step (h).

Suitable mono-auxotrophic mutants for use in the process of the invention are known to those skilled in the art having been disclosed in U.S. Application Ser. No. 666,579, filed Oct. 30, 1984 by Stroman et al. and assigned to Phillips Petroleum Company, the disclosure of which is hereby incorporated by reference. Exemplary mono-auxotrophic mutants include NRRL Y-15851 (GS115), a histidine requiring mutant, NRRL Y-18041 (GS190), an arginine requiring mutant, and the like.

To prepare Pichia spheroplastis, the cells are contacted with a sulfhydryl group reducing agent, such as for example, dithiothreitol or β-mercaptoethanol and a cell wall degrading reagent. An example of a specific solution containing a sulfhydryl group reducing agent is the 0.7% (v/v) β-mercaptoethanol solution buffer described in the Examples. Enzymatic digestion of the cell walls is accomplished by contacting the strains to be spheroplasted with any of the cell wall degrading reagents known to those of skill in the art, such as for example, Zymolyase (60,000 units/g; Miles Laboratories), Glusulase (Endo Laboratories), and the like. A wide variety of temperatures, contact times and dosage levels for cell wall degrading reagents are operable. Generally, in the range of about 10 μg to 400 μg of Zymolyase or 600-20,000 units of Glusulase per 10 mL of cell suspension are employed for spheroplast formation. Preferably about 40-200 μg of Zymolyase or 1,000-5,000 units of Glusulase 10 mL of cell suspension is employed. Temperature is generally maintained at about 25° C. or above, but less than about 35° C. Preferably, temperature is maintained at about 30° C. Contact time is generally at least about 15 minutes and usually no greater than about 60 minutes. While many buffered media are suitable, it is essential that cells to be converted to spheroplasts be suspended in a buffer which is iso-osmotic with the cells, such as, for example, 0.7M MgSO$_4$, or SCE buffer (sorbitol/citrate/EDTA; see Examples for recipe).

Spheroplasts of a first and a second monoauxotrophic strain of Pichia pastoris are prepared as described above, centrifuged, and the spheroplast pellets are then resuspended in the presence of a cell fusion promoting agent, e.g., about 1 mL of the spheroplast fusion media (CaCl$_2$, polyethylene glycol, DMSO solution) per spheroplast-containing pellet. The two spheroplast suspensions are mixed, and maintained at about 20°-30° C. for 5-30 minutes.

The mixed spheroplasts are then treated under cell wall regenerating conditions. Cell wall regenerating conditions comprise plating spheroplasts on to plates containing regeneration agar as medium. A typical regeneration agar provides a balanced osmotic media and comprises:

MgSO$_4$—about 0.35M
dextrose—about 0.1M
yeast nitrogen base—about 7 g/L
Bacto-agar—about 3%

Plates are then incubated—about 25°-35° C. for about 3-5 days.

Only prototrophs can grow on the regeneration agar-containing plates; parental auxotrophic strains are incapable of growth on this medium and thus serve as an internal control. The frequency of recovery of prototrophs was very low on the control plates, which contained either of the mono-auxotrophic parents, when compared to the experimental plates, which contained both of the mono-auxotrophic parents. The prototrophs were transferred to minimal master plates and then sporulated by transferring them to presporulation plates for 24 hours and then transferring to sporulation plates and incubating the plates for 3-5 days. The resulting 4-spored asci are either dissected, or cells are removed from sporulation plates, resuspended in phoshate buffered media and exhaustively digested with a cell wall degrading reagent. As a result of the latter treatment, vegetative cells are destroyed, and only random spores remain to be germinated and grown. While the latter method is preferred for rapid sample generation, the former method (i.e., dissection of the 4-spored asci) is preferred when a statistical population of segregants is desired. The resulting colonies are finally screened for the presence of double auxotrophic mutants.

The screening of the individual spores derived from the fused cells is carried out as follows. The spores are germinated and grown up on rich media at about 25°-35° C. for about 2-5 days, then plated on a master plate, from which replicate plates are prepared. One replicate plate contains as medium a minimal media plus the biosynthetic product in which the first mono-auxotrophic mutant is defective, while another replicate plate contains as medium a minimal media plus the biosynthetic product in which the second mono-auxotrophic mutant is defective. The double auxotrophic mutants are identified as those cells which are capable of growth only on rich medium but which are not capable of growth on either of the minimal media supplemented with only one of the biosynthetic products in which the mono-auxotrophic strains were deficient. The colonies that correspond on the master plate to those cells which did not grow under minimal feed conditions but which did grow on rich medium were then picked for further characterization.

In accordance with another embodiment of the present invention, a mating process for producing double auxotrophic mutants of yeast strains of the species Pichia pastoris is provided. The mating process of the invention comprises the following steps:

(a) suspending together in rich media colonies of a first and a second mono-auxotrophic mutant yeast strain of the species Pichia pastoris ;

(b) plating the suspension containing said first and second mono-auxotrophic mutant yeast strains prepared in accordance with step (a) on presporulation agar and maintaining plates at about 30° C. for about 12-48 hours, preferably about 24 hours;

(c) replica plating the cells produced in accordance with step (b) onto sporulation agar and maintaining the resulting plates at about 30° C. for about 8-48 hours, preferably about 24 hours;

(d) replica plating the cells produced in accordance with step (c) onto minimal agar and maintaining at 25°-35° C. for 1-5 days, or until colonies are visible;

(e) suspending individual prototrophic colonies obtained from step (d) in rich media;

(f) plating the suspension produced in accordance with step (e) on presporulation agar and maintaining the resulting plates at about 30° C. for about 12-48 hours;

(g) replica plating the cells produced in accordance with step (f) onto sporulation agar and maintaining the resulting plates at about 30° C. for 3-5 days;

(h) alternatively (1) dissecting the 4-spored asci produced in accordance with step (g), or (2) removing the cells from the sporulation plates, resuspending the cells in phosphate buffered media and exhaustively digesting the suspended cells with a cell wall degrading reagent;

(i) then germinating and growing each spore in rich media at about 25°-35° C. for about 48 hours; and thereafter (j) screening the colonies prepared in accordance with step (i) for double auxotrophic mutants.

Suitable mono-auxotrophic mutants for use in the process of the invention are known to those skilled in the art having been disclosed in U.S. Application Ser. No. 666,579, filed Oct. 30, 1984 by Stroman et al. and assigned to Phillips Petroleum Company, the disclosure of which is hereby incorporated by reference. Exemplary mono-auxotrophic mutants include NRRL Y-15851 (GS115), a histidine requiring mutant, NRRL Y-18014 (GS190), an arginine requiring mutant, and the like.

The cells to be mated are first suspended in a rich media, such as for example, YPD (see examples for recipe) and other similar media as well known to those of skill in the art. The suspended cells are plated on presporulation agar, and maintained at about 30° C. for 12 up to 48 hours. A typical formulation for presporulation agar is set forth below in the example section.

Once grown on presporulation agar, cells are replica plated to sporulation agar, then maintained at about 30° C. for about 8-24 hours. A typical sporulation medium is set forth below in the example section.

Cells grown on the sporulation agar are then replica plated and germinated on minimal agar at about 25°-35° C. for about 1-5 days. A typical formulation for minimal agar is:

1-8% dextrose
0.1-2% yeast nitrogen base, minus amino acids, and
1.5-4% agar.

A preferred formulation for minimal agar is set forth in the examples.

The resultant colonies are suspended in rich media, such as, for example, YPD, plated on presporulation agar as described hereinabove and maintained at about 30° C. for about 12-48 hours, then replica plated onto sporulation agar and maintained at about 30° C. for about 3-5 days. The resulting 4-spored asci are either dissected, or cells are removed from sporulation plates, resuspended in phosphate buffered media and exhaustively digested with a cell wall degrading reagent. As a result of the latter treatment, vegetative cells are destroyed, and only random spores remain to be germinated and grown. While the latter method is preferred for rapid sample generation, the former method (i.e., dissection of the 4-spored asxi) is preferred when a statistical population of segregants is desired. The resulting colonies are finally screened for the presence of double auxotrophic mutants.

The screening procedure involves germinating and growing the spores up on rich medium at about 25°-35° C. for about 3-5 days, then replica plating onto two different plates, one plate containing synthetic complete media less the bio-synthetic product in which the first mono-auxotrophic mutant is defective, while the other plate contains synthetic complete media less the biosynthetic product in which the second mono-auxotrophic mutant is defective. The double auxotrophic mutants are identified as those colonies which grow on the rich media, but are incapable of growth on either of the synthetic complete media lacking the biosynthetic products in which either of the mono-auxotrophic mutants, from which the double auxotroph is derived, is defective.

Alternatively, the screening procedure can entail replica plating the colonies grown on rich media onto two different plates, the first of which contains minimal media plus the biosynthetic product in which the first monoauxotrophic mutant is defective and the second plate contains minimal media plus the biosynthetic product in which the second mono-auxotrophic mutant is defective. As in the previously described screening procedure, the double auxotrophic mutants are identified as those colonies which grow on the rich media, but do not grow on either of the supplemented minimal media plates.

The production of double auxotrophic mutants of *Pichia pastoris* provides useful hosts for the production of recombinant DNA products by yeast. The existence of two auxotrophic mutations in the same cell allows transformation with transforming DNA which includes a variety of marker genes, as well as allowing the use of a variety of selective growth conditions to facilitate identification and isolation of the desired transformants.

The invention will now be described in greater detail by reference to the following non-limiting examples.

EXAMPLES

The buffers and solutions employed in the following examples have the composition given below:

| | |
|---|---|
| 1 M Tris buffer | 121.1 g Tris base in 800 mL of $H_2O$; adjust pH to the desired value by adding concentrated (35%) aqueous HCl; allow solution to cool to room temperature before final pH adjustment; dilute to a final volume of 1 L. Appropriate dilutions are made from this stock solution. |
| YPD Medium | 1% Bacto-yeast extract<br>2% Bacto-peptone<br>2% Dextrose |
| SCE Buffer | 9.1 g Sorbitol<br>1.47 g Sodium citrate<br>0.168 g EDTA<br>50 mL $H_2O$<br>pH to 5.8 with HCl |
| Spheroplast Fusion Medium | 30% w/v PEG8000<br>15% w/v DMSO<br>100 mM $CaCl_2$ |
| Regeneration Agar | 0.35 M $MgSO_4$<br>2% dextrose<br>0.675% yeast nitrogen base (minus amino acids)<br>3% bacto-agar |
| YEPD Agar | 2% dextrose<br>2% peptone |

| | -continued |
|---|---|
| | 1% yeast extract |
| | 2% agar |
| Presporulation Agar | 5% dextrose |
| (GNAP) | 2% peptone |
| | 1% yeast extract |
| | 0.5% agar |
| | 2.3% nutrient agar |
| Sporulation Agar | 0.5% sodium acetate (anhydrous) |
| | 1% KCl |
| | 2% agar |
| Minimal Agar | 2% dextrose |
| | 0.675% yeast nitrogen base |
| | (minus amino acids) |
| | 2% agar |
| SC (synthetic complete) | 2% dextrose |
| Agar | 0.675% yeast nitrogen base |
| | (minus amino acids) |
| | 2% agar |
| | amino acid suplementation as follows: |

| Supplemented Amino Acid | Final Concentration mg/L |
|---|---|
| adenine sulfate | 20 |
| uracil | 20 |
| L-tryptophan | 20 |
| L-histidine-HCl | 20 |
| L-arginine-HCl | 20 |
| L-methionine | 20 |
| L-tyrosine | 30 |
| L-leucine | 30 |
| L-isoleucine | 30 |
| L-lysine-HCl | 30 |
| L-phenylalanine | 50 |
| L-glutamic acid | 100 |
| L-aspartic acid | 100 |
| L-valine | 150 |
| L-threonine | 200 |
| L-serine | 375 |

| | |
|---|---|
| SC-arg Agar | As SC agar, but no arginine amino acid supplement |
| SC-his Agar | As SC agar, but no histidine amino acid supplement |

EXAMPLE I *Pichia pastoris* Fusion Procedure

A. Cell Growth

1a. A colony of *Pichia pastoris* GS115 (NRRL Y-1581) was inoculated at about 10 mL of YPD medium and shake cultured at 30° C. for 12-20 hrs.

1b. A colony of *Pichia pastoris* GS190 NRRL Y-18014) was inoculated into about 10mL of YPD medium and shake cultured at 30° C. for 12-20 hours.

2. Cultures were harvested when $OD_{600}$ was about 0.2–0.3 (after approximately 16-20 hrs) by centrifugation at 1500 g for 5 minutes.

B. Preparation of Speroplasts

1. Cells were washed once in 10 mL of sterile water by centrifugation at 1500 g for 5 minutes.

2. The cells were resuspended in 10 mL of 50 mM tris-HCl, pH 7.5, 0.7M $MgSO_4$.

3. 200 μL glusulase (to give a final concentration of 2% v/v) and 10 μL β-mercaptoethanol (to give a final concentration of 0.7% v/v) were added.

4. Cells were incubated at 30° C. for 90 minutes with gentle shaking.

Since the preparation of spheroplasts is a critical step in the fusion procedure, spheroplast formation was monitored as follows: 100 μL aliquots of cells were added to 900 μL of 1M Sorbitol before or just after the addition of glusulase and at various times during the incubation period. The incubation was stopped at the point where cells lyse in SDS but not in sorbitol.

5. Intact cells were separated by low speed centrifugation at 400g for 5 minutes. The supernatant containing the spheroplasts was then transferred to fresh tubes.

6. The spheroplast suspension was diluted with 50 mM Tris-HCl, pH 7.5, to decrease the $MgSO_4$ concentration to 0.25M.

C. Fusions of spheroplastis

1. Spheroplasts were centrifuged at 1000g for 5 minutes and resuspended in 1 mL of spheroplast fusion medium.

2. A 0.5 mL volume of each mono-auxotrophic spheroplast preparation was mixed together and the volume in the original tubes was brought back to 1 mL with spheroplast fusion medium. The tubes with the mono-auxotropic spheroplasts served as controls for reversion to prototrophy.

3. All tubes were incubated for 30 minutes at room temperature.

D. Plating of Fusion Samples 1. 20 mL regeneration agar per plate was poured at least 2 hours before the fusion samples were ready.

2. 1:10 and 1:100 dilutions of each sample were prepared in 1 mL volumes of the PEG solution. 0.1 mL volumes from each tube/plate were used for regeneration of spheroplasts.

3. Plates were incubated at 30° C. for 3-5 days.

E. Screening of Cell Fusions

The fused cells obtained employing the above fusion procedure were screened, and double auxotrophic mutants isolated therefrom as follows:

After 3-5 days growth on regeneration agar, prototrophic colonies resulting from the fusions were transferred to minimal medium master plates. The master plates were incubated for 2 days and isolates that regrew on the master plates were sporulated by replica plating on to presporulation plates for 24 hours and then on to sporulation plates which were incubated at 30° C. for 5 days. The 4-spored asci that resulted were isolated and dissected by micromanipulation on YPD plates. Alternatively, instead of dissecting the 4-spore asci, the cells can be removed from the sporulation plates, washed twice with 0.1M sodium phosphate buffer, pH 7.5 and resuspended in 2.7 mL of sodium phosphate buffer. To the suspension was added 3 μL β-mercaptoethanol (0.1% final), 60 μL glusulase (2% final), 300 μL of a zymolayse 60,000 stock solution containing 5 mg/mL in phosphate buffer (0.5 mg/mL final) and the mixture was digested for 5 hours at 30° C. with occasional shaking. The resultant spore preparation was sonicated three times for 15 seconds and harvested by centrifugation at 3000×g for 10 minutes. The resultant pellet was washed twice with a 0.2% Tween 80 solution and resuspended in 0.1M phosphate buffer at approximately $10^7$ spores/mL. Single spores were germinated after plating on YEPD agar plates. In some cases, due to clumping of the spores, separation into single spores was accomplished using a micromanipulator.

The YEPD agar plates were incubated until colonies from the spores reached sufficient size to be transferred to duplicate YEPD master plates. One of each YEPD master was then used for replica plating to synthetic complete medium plates lacking one of the single auxotrophic requirements (e.g. synthetic complete medium minus arginine and synthetic complete medium minus histidine). The results of this screen were used to identify prototrophs by their growth on both plates; mono-auxotrophs grew on only one of the plates, and double-auxotrophs failed to grow on either of the plates. Double auxotrophic isolates were then transferred to YEPD or synthetic complete plates for storage.

The fusion procedure described hereinabove utilizing the mono-auxotrophic mutants P. pastoris GS115 (his4) and P. pastoris GS190 (arg4), led to the isolation of a double auxotrophic mutant having the phenotype arg⁻ his⁻. This double auxotrophic mutant has been given the laboratory designation PPF1. P. pastoris strain PPF1 has been deposited with the Northern Regional Research Center of the United States Department of Agriculture in Peoria, Illinois to ensure public access to the strain upon issuance of this application as a patent. Strain PPF1 has been given the accession number NRRL Y-18017.

EXAMPLE II

Cross Mating of *Pichia pastoris* Auxotrophs

The mono-auxotrophic strains GS115 (his4⁻) and GS190 (arg4⁻) were crossed as follows:

Single colonies of each of the two auxotrophic mutants were resuspended in 100 μL of YPD, mixed thoroughly, and spread on presporulation (GNAP) plates. Twenty-four hours after plating on GNAP, cells were replica-plated onto sporulation agar. Eight hours after plating on sporulation agar, cells were replica-plated onto minimal media. These plates were incubated at 30° C. for 1.5-2 days, until colonies were seen.

Prototrophic colonies from minimal plates were sporulated by subjecting them to a regimen similar to that described above for mating, e.g., a single colony was dispersed in YPD, plated on GNAP, and replica-plated onto sporulation agar after 24 hours on GNAP. After 3 days on sporulation agar, 4-spored asci were dissected on YEPD plates which then were put at 30° C. to germinate. Alternatively, the exhaustive digestion procedure for spore preparation described above can be employed instead of the dissection procedure. Wild type segregants, as well as single and double auxotrophs, were identified by replica-plating onto SC-arg and SC-his media.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A yeast cell of the species *Pichia pastoris* as a host capable of being transformed with recombinant DNA material, wherein said host is defective in histidinol dehydrogenase activity and in argininosuccinate lyase activity.

2. A yeast in accordance with claim 1 wherein said yeast cell is *Pichia pastoris* NRRL Y-18017 (PPF1).

* * * * *